US011304901B2

(12) United States Patent
Huang et al.

(10) Patent No.: US 11,304,901 B2
(45) Date of Patent: Apr. 19, 2022

(54) LIPOSOME FORMULATION OF FLUTICASONE FUROATE AND METHOD OF PREPARATION

(71) Applicant: ANOVENT PHARMACEUTICAL (U.S.), LLC, Newark, NJ (US)

(72) Inventors: Cai Gu Huang, Shrewsbury, MA (US); Hailong Zhang, Shanghai (CN); Abid Hussain, Shanghai (CN)

(73) Assignee: ANOVENT PHARMACEUTICAL (U.S.), LLC, Newark, NJ (US)

( * ) Notice: Subject to any disclaimer, the term of this patent is extended or adjusted under 35 U.S.C. 154(b) by 0 days.

(21) Appl. No.: 17/001,889

(22) Filed: Aug. 25, 2020

(65) Prior Publication Data

US 2021/0059937 A1 Mar. 4, 2021

Related U.S. Application Data

(60) Provisional application No. 62/892,567, filed on Aug. 28, 2019.

(51) Int. Cl.
*A61K 9/127* (2006.01)
*A61K 31/58* (2006.01)
(Continued)

(52) U.S. Cl.
CPC ............ *A61K 9/127* (2013.01); *A61K 9/1277* (2013.01); *A61K 31/58* (2013.01); *A61K 47/02* (2013.01);
(Continued)

(58) Field of Classification Search
CPC ...................................................... A61K 9/127
See application file for complete search history.

(56) References Cited

U.S. PATENT DOCUMENTS 6,777,400 B2 8/2004 Biggadike et al.
7,101,866 B2 9/2006 Biggadike et al.
(Continued)

FOREIGN PATENT DOCUMENTS

CN 101601650 A 12/2009
CN 105012237 A * 11/2015
(Continued)

OTHER PUBLICATIONS

NM Nirale, RD Vidhate, MS Nagarsenker. "Fluticasone Propionate Liposomes for Pulmonary Delivery." Indian Journal of Pharmaceutical Sciences, vol. 71(6), Nov.-Dec. 2009, accessed at https://www.ncbi.nlm.nih.gov/pmc/articles/PMC2846484/?report=printable on Nov. 5, 2020, 5 pages. (Year: 2009).*
(Continued)

*Primary Examiner* — Isaac Shomer
(74) *Attorney, Agent, or Firm* — Parker Poe Adams & Bernstein LLP

(57) ABSTRACT

The present invention is directed to a liposomal formulation having a lipid ingredient encapsulating fluticasone furoate, and a method for preparing the liposomal formulation. The liposome formulation comprises a lipid and a sterol. The method of preparing the liposomes comprises the steps of (1) mixing fluticasone furoate with lipid ingredients comprising a lipid and a sterol, (2) injecting the mixture into normal saline solution, and (3) ultrafiltering and concentrating the resulting solution. This preparation method can produce a liposome formulation having desirable properties and compositions, for example, the ratio of the lipid ingredient, the drug to lipid ratio, and the pH value, which is suitable for nebulization inhalation.

14 Claims, 4 Drawing Sheets

(51) Int. Cl.
*B01F 21/00* (2022.01)
*A61K 47/02* (2006.01)
*A61K 47/22* (2006.01)
*A61K 47/20* (2006.01)

(52) U.S. Cl.
CPC .............. *A61K 47/20* (2013.01); *A61K 47/22* (2013.01); *B01F 21/02* (2022.01)

(56) References Cited

U.S. PATENT DOCUMENTS

| | | | |
|---|---|---|---|
| 8,148,353 | B2 | 4/2012 | MacDonald et al. |
| 2007/0269502 | A1* | 11/2007 | Pliura ..................... A61P 43/00 424/450 |
| 2009/0047336 | A1 | 2/2009 | Yang et al. |
| 2009/0104256 | A1* | 4/2009 | Gupta ..................... A61P 11/12 424/450 |
| 2009/0324699 | A1* | 12/2009 | Preswetoff-Morath ..................... A61K 9/0043 424/450 |
| 2014/0335153 | A1 | 11/2014 | Allen et al. |
| 2017/0050945 | A1* | 2/2017 | Chen ........................ A61K 9/14 |
| 2017/0189424 | A1* | 7/2017 | Barnes ................. A61K 9/0075 |
| 2018/0298057 | A1 | 10/2018 | Koval et al. |

FOREIGN PATENT DOCUMENTS

| | | | |
|---|---|---|---|
| CN | 111789816 | A * | 10/2020 |
| CN | 111789816 | A | 10/2020 |
| WO | WO-2014/096032 | A1 | 6/2014 |
| WO | WO-2016/142708 | A2 | 9/2016 |

OTHER PUBLICATIONS

Keith Biggadike. "Fluticasone furoate/fluticasone propionate—different drugs with different properties." The Clinical Respiratory Journal, ISSN 1752-6981, 2011, pp. 183-184. (Year: 2011).*

Amir Amani, Peter York, Henry Chrystyn, and Brian J. Clark. "Evaluation of a Nanoemulsion-Based Formulation for Respiratory Delivery of Budesonide by Nebulizers." AAPS PharmSciTech, vol. 11, No. 3, Sep. 2010, pp. 1147-1151. (Year: 2010).*

Mindaugas Rudokas, Mohammad Najlah, Mohamed Albed Alhnan, Abdelbary Elhissi. "Liposome Delivery Systems for Inhalation: A Critical Review Highlighting Formulation Issues and Anticancer Applications." Medical Principles and Practice, vol. 25 (Suppl 2), 2016, pp. 60-72. (Year: 2016).*

Google Patents. English Translation of CN111789816A. https://patents.google.com/patent/CN111789816A/en?oq=CN111789816 accessed Jul. 12, 2021, originally published in Chinese on Oct. 20, 2020, pp. 1-8. (Year: 2020).*

Google Patents. English Translation of CN 105012237 A. https://patents.google.com/patent/CN105012237A/en?oq=fluticasone+furoate+suspension accessed Oct. 22, 2021, 7 printed pages, originally published in Chinese on Nov. 4, 2015. (Year: 2015).*

Pedro Giavina-Bianchi, Rosana Agondi, Rafael Stelmach, Alberto Cukier. "Fluticasone furoate nasal spray in the treatment of allergic rhinitis." Therapeutics and Clinical Risk Management, vol. 4(2), 2008, pp. 465-472. (Year: 2008).*

Written Opinion and International Search Report issued in PCT/US20/47734 dated Jan. 22, 2021.

English translation of CN111789816A is provided.
English translation of CN101601650A is provided.

* cited by examiner

LIPOSOME FORMULATION OF FLUTICASONE FUROATE AND METHOD OF PREPARATION

PRIORITY STATEMENT

This preparation method can produce a liposome formulation, which has useful features, for example, the ratio of the lipid ingredients and the pH value.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

The use of identical or similar reference numerals in different figures denotes identical or similar features.

DETAILED DESCRIPTION OF THE INVENTION

Figure 1:
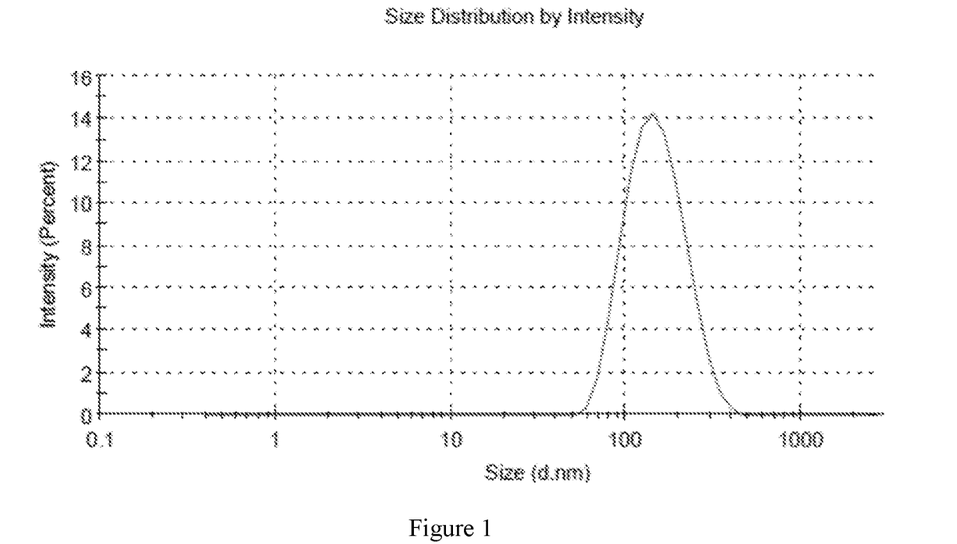
FIG. 1 is a graph of the size distribution of fluticasone furoate liposome of sample 1 in example 2.
Figure 2:
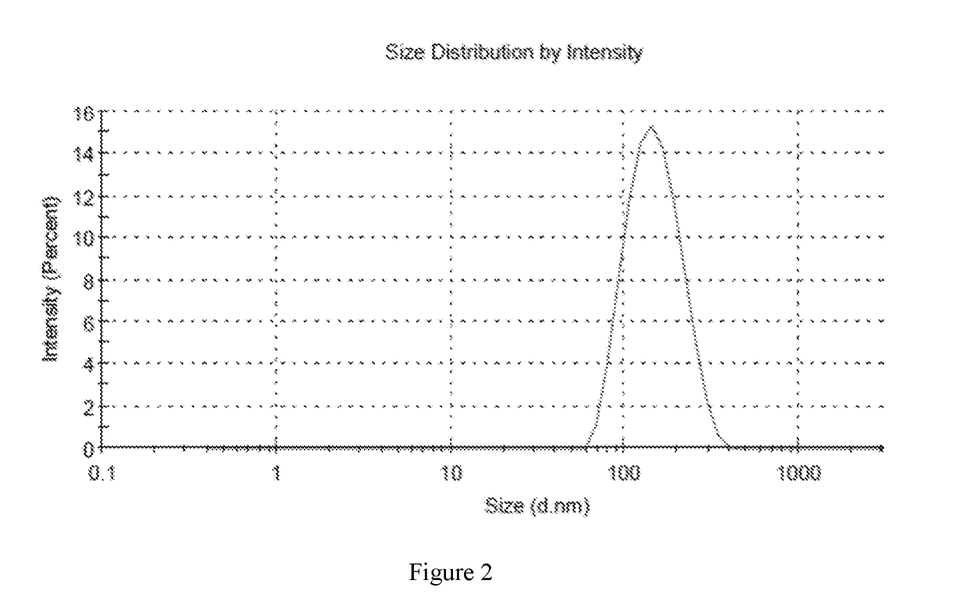
FIG. 2 is a graph of the size distribution of fluticasone furoate liposome of sample 2 in example 2.
Figure 3:
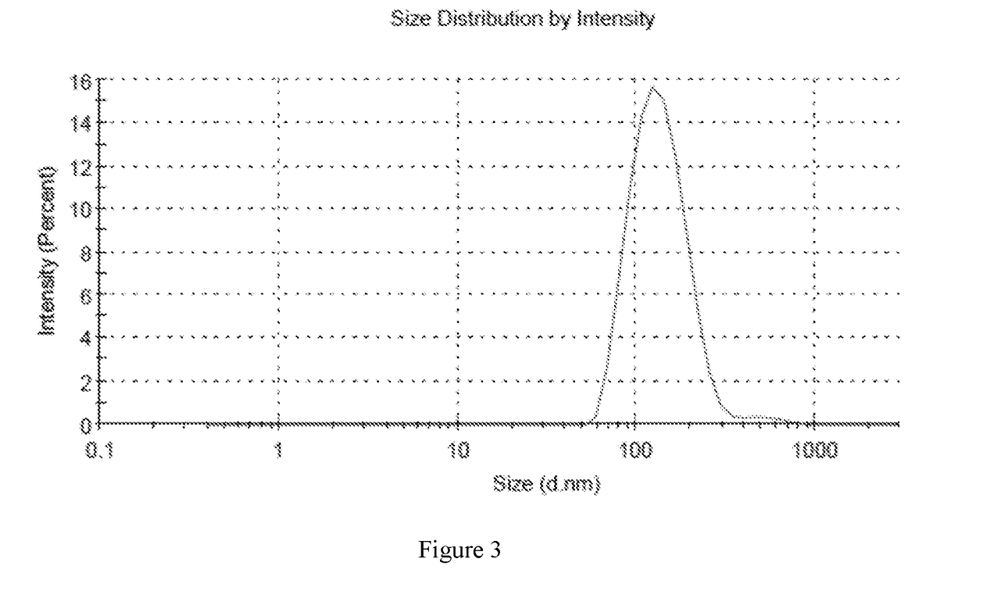
FIG. 3 is a graph of the size distribution of fluticasone furoate liposome of sample 3 in example 2.
Figure 4:
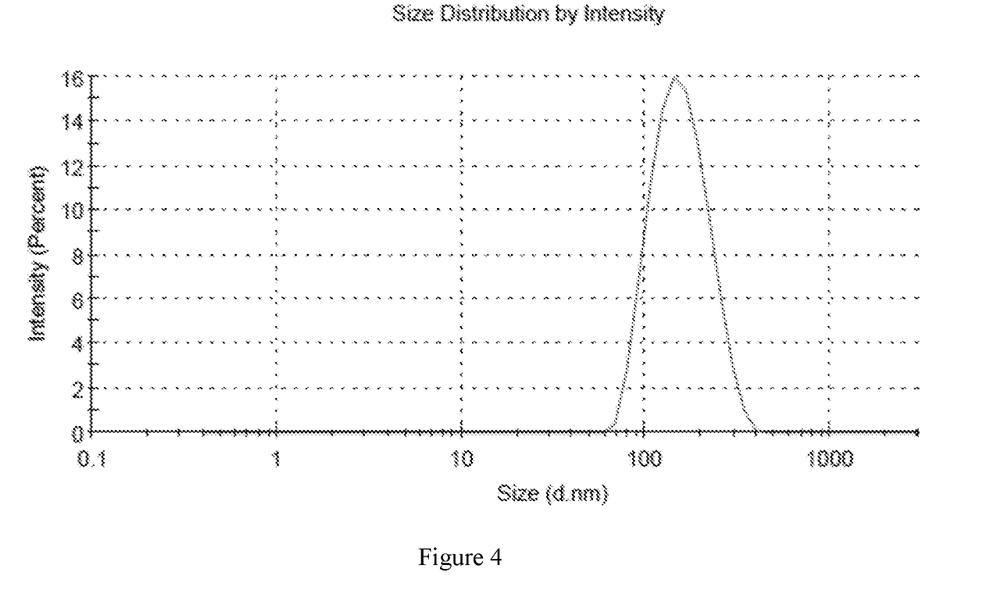
FIG. 4 is a graph of the size distribution of fluticasone furoate liposome of sample 4 in example 2.
Figure 5:
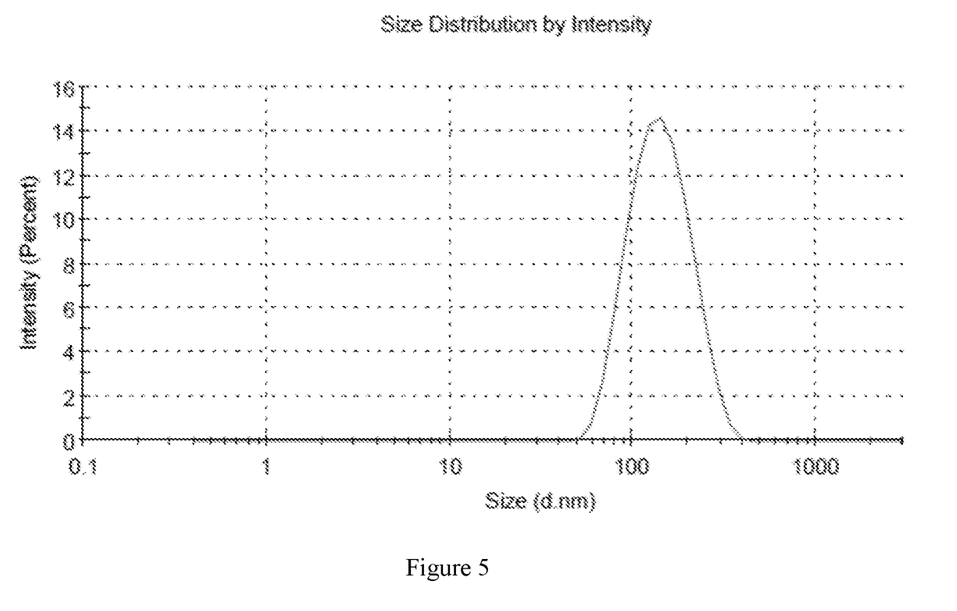
FIG. 5 is a graph of the size distribution of fluticasone furoate liposome of sample 5 in example 2.
Figure 6:
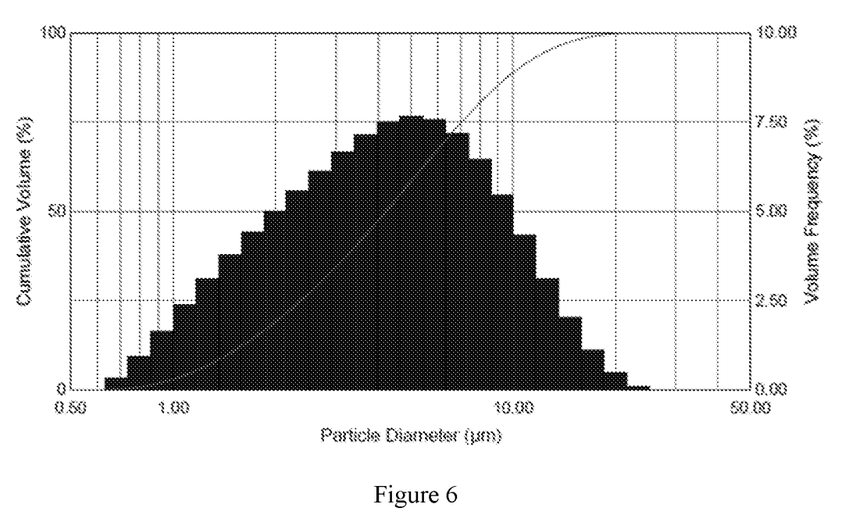
FIG. 6 is a graph of particle size distribution of droplets formed using a compressed air nebulizer.
Figure 7:
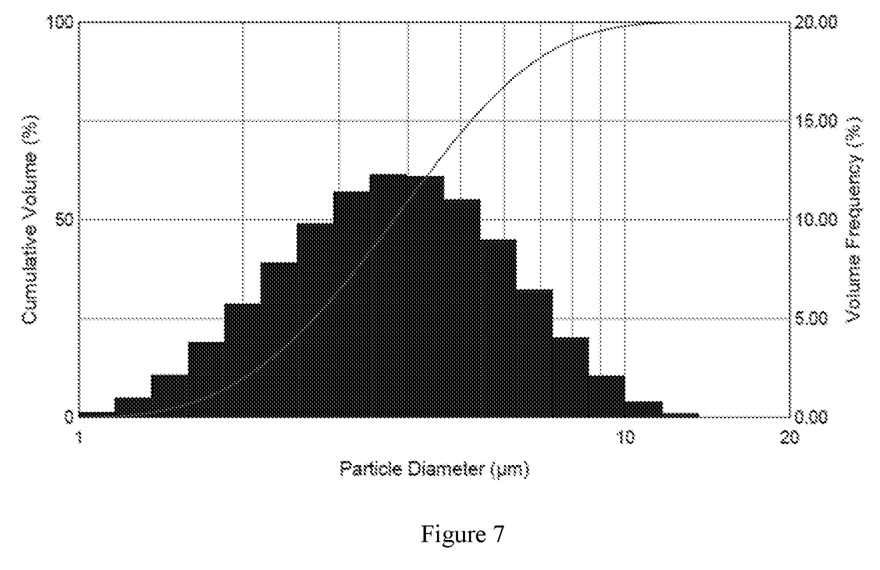
FIG. 7 is a graph of particle size distribution of droplets formed using an ultrasonic vibrating mesh nebulizer.

For purposes of describing the invention, reference now will be made in detail to embodiments and/or methods of the invention, one or more examples of which are illustrated in or with the drawings. Each example is provided by way of explanation of the invention, not limitation of the invention. In fact, it will be apparent to those skilled in the art that various modifications and variations can be made in the present invention without departing from the scope or spirit of the invention. For instance, features or steps illustrated or described as part of one embodiment can be used with another embodiment or steps to yield a still further embodiments or methods. Thus, it is intended that the present invention covers such modifications and variations as come within the scope of the appended claims and their equivalents.

The present invention relates to a liposomal formulation and a method for preparing the liposomal formulation. The formulation comprises a plurality of liposomes encapsulating fluticasone furoate. The physical characteristics of each liposome facilitates stability and effectiveness of the liposomal formulation. The formulation is characterized by liposomes which are substantially uniform in size and shape. In addition, the invention provides an efficient method for preparing the liposome formulation, which can meet the needs of large-scale preparation.

As used herein, the term "liposome" refers to microscopic closed vesicles having an internal phase enclosed by lipid bilayer. In the present invention, liposome includes small single-membrane liposomes, large single-membrane liposomes, still larger single-membrane liposomes, multilayer liposomes having multiple concentric membranes, liposomes having multiple membranes that are not concentric, but irregular, etc.

The term "liposome internal phase" refers to an aqueous region enclosed in the lipid bilayer of the liposome, and is used with the same meaning as "internal water phase" and "liposome internal water phase."

The present invention relates to a liposome formulation. Different liposome ingredients may be used to form the liposome of the invention. Preferably, the lipid ingredient is a non-toxic biocompatible lipid, for example, lipids prepared from phosphatidyl-choline, phosphoglycerol, and/or cholesterol, in an embodiment, the lipid ingredient may comprise dipalmitoylphosphatidylcholine (DPPC), diastearoylphosphatidylcholine (DSPC), diastearoylphosphatidylglycerol (DSPG) and, cholesterol, or combinations thereof. In one embodiment, the lipid ingredient comprises DPPC and cholesterol, which may be present in a molar ratio of about 1:1.

As used herein, the term "lipid ingredients" refers to a sterol and a lipid. For example, cholesterol and diastearoylphosphatidylcholine (DSPC), cholesterol and dipalmitoylphosphatidylcholine (DPPC), etc. In an embodiment the lipid and sterol may be present in a molar ratio of about 1:1, such as from about 0.6:1 to about 1.4:1, more particularly such as from about 0.8:1 to about 1.2:1 (lipid:sterol).

The liposome formulation is characterized by liposomes having a desirable composition and physical characteristics. The liposome of the present invention comprises lipid ingredients encapsulating fluticasone furoate. According to the invention, the lipid is selected from the group consisting of phosphatidylcholine (PC), phosphatidic acid (PA), phosphatidylethanolamine (PE), phosphatidylglycerol (PG), phosphatidylserine (PS), phosphatidylinositol (PI), dimyristoyl phosphatidyl choline (DMPC), distearoylphosphatidyl choline (DSPC), dipalmitoyl phosphatidyl choline (DPPC), dimyristoyl phosphatidyl glycerol (DMPG), distearoylphosphatidyl glycerol (DSPG), dioleoyl phosphatidyl glycerol (DOPG), dipalmitoylphosphatidyl glycerol (DPPG), dimyristoyl phosphatidyl serine (DRIPS), distearoyl phosphatidyl serine (DSPS), dioleoyl phosphatidyl serine (DOLS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE), dioleoyl-phosphatidyl ethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), distearoylphosphatidylcholine (DSPC), dioleoylphosphatidylcholine (DOPC), dipalmitoylphosphatidylcholine (DPPC), palmitoyloleoylphosphatidylcholine (POPC), and palmitoyloleoyl-phosphatidylethanolamine (POPE).

According to the invention, the sterol is at least one kind selected from cholesterol.

The lipid ingredients may comprise a lipid and cholesterol. In an embodiment, the lipid ingredients are selected from dipalmitoylphosphatidylcholine (DPPC) and cholesterol in the range of about 0.6:1 to about 1.4:1 (DPPC:cholesterol) in molar ratios. In another embodiment the DPPC and cholesterol may be present in a molar ratio of about 1:1, more particularly such as from about 0.8:1 to about 1.2:1 (DPPC:cholesterol).

Within the scope of the present invention, the "drug to lipid ratio" refers to the relative amounts of the drug to the lipid ingredients by mass that comprise the liposome and/or formulation. In one embodiment, the liposome has a drug to lipid ratio between about 1:10 and about 1:40 by weight. In another embodiment, the liposome has a drug to lipid ratio between about 1:10 and about 1:20 by weight.

The pH affects the properties of the liposomal formulation in the solvent. The pH affects the stability, drug leakage rate from the liposome, and drug encapsulation capability of the liposome formulation. The pH value of the liposomal formulation is from about 4.0 to about 7.0. In one embodiment, the liposomal formulation has a pH value in the range of about 5.0 to about 6.0.

According to the invention, the liposome formulation comprises a plurality of liposomes which have the characteristics described above and being substantially uniform in size and shape. The liposomes may be in the size range of about 50 to about 1000 nm. In an embodiment, the size range is about 70 to about 800 nm; more particularly, the size range is about 70 to about 500 nm. In an embodiment, the size of the liposome is about 150 nm. In another embodiment, the size of the liposome is about 130 nm.

According to the present invention, the liposome formulation may be formulated using one or more physiologically acceptable carriers comprising excipients and auxiliaries known in the art.

The liposomal formulation may be administered by any route which effectively transports the liposomes to the appropriate site of action. One effective route of administration is by inhalation. Other suitable routes of administration may include intramuscular, subcutaneous and intraperitoneal.

According to the invention, the liposome formulation may comprise an antioxidant selected from the group consisting of water-soluble antioxidants and oil-soluble antioxidants. Examples of oil-soluble antioxidants include, but are not limited to, alpha-tocopherol, alpha-tocopherol succinate, alpha-tocopherol acetate, and mixtures thereof. Examples of water-soluble antioxidants include, but are not limited to, ascorbic acid, sodium bisulfite, sodium sulfite, sodium pyrosulfite, L-cysteine, and mixtures thereof.

The process for making the liposome and liposomal formulation permits manipulation of the physical characteristics described above, as well as control of certain process parameters, for example, solvent composition and solvent ratios and vesicle preparation temperature. The preparation of the liposome formulation comprises the steps of: (1) mixing fluticasone furoate with lipid ingredients comprising a lipid and a sterol, (2) injecting the mixture into normal saline solution to form liposome vesicles, and (3) ultrafiltration and concentration of the resulting liposome vesicle-containing solution.

This preparation method has the advantage that the physiological and chemical features of the liposome can be controlled and monitored. For example, the drug to lipid ratio may be managed by the selection of the lipid ingredients used to form the liposome or the amount of lipids added to the dissolved active agent. Increasing the amount of lipid ingredients decreases the drug to lipid ratio, and vice versa.

The first step comprises mixing fluticasone furoate and lipid ingredients in a solvent to form a lipid solution. In many cases, the lipid solvent is heated to a temperature in the range of about 40° C. to about 80° C. to facilitate solubilization of the fluticasone furoate and lipid ingredients.

In a preferred embodiment, the lipid solvent is heated to about 50° C. to facilitate solubilization of the fluticasone furoate and lipid ingredients.

The second step comprises injecting the mixture into normal saline solution to form liposome vesicles. The second step may comprise a hydrophilic solution to form liposome vesicles in addition to, or in place of, the normal saline described above.

The mixture of fluticasone furoate and lipid ingredients is added or injected into the normal saline, which may be at about ambient temperature. The normal saline may be optionally heated during the process.

The third step comprises ultrafiltration and concentration. Different types of filtration membranes may be used during the ultrafiltration process. In one embodiment, the ultrafiltration step uses a hollow fiber membrane, where the formulation is pushed through the open hollow cores of the fiber, and the micromolecules are filtered through the outer membrane of the fiber, while the relatively larger liposomes remain within the fiber. For a new hollow fiber cartridge, the cartridge is typically filled with 100% alcohol for one hour. In an embodiment, the cartridge may be soaked for over one hour.

Following the ultrafiltration step, the process may further include a dialyzing step, wherein the formulation is dialyzed against a volume of a buffered solution. In one embodiment, the buffer solution is a normal saline. Other buffer additives are known in the art, including, but not limited to, sucrose, glycine, sodium chloride, succinate, or combinations thereof. The buffer solution preferably reflects the environment of the final formulation that is external to the liposome. Preferably, the buffer solution is isotonic and non-toxic to cells. The buffer solution may be filtered to further reduce contaminants and may be prepared in advance of the preparation process.

The lipid ingredients may be in the form of a solution containing the desired starting amount of the lipid ingredient in a volume of one or more lipid solvents. Any suitable lipid ingredient and lipid solvent may be used. For example, the lipid ingredients may comprise DPPC and cholesterol in a molar ratio of about 1:1, prior to liposome formation. The resultant liposome formed according to this combination of lipids may also have about a 1:1 molar ratio of DPPC and cholesterol.

Examples of lipid solvents include, but are not limited to, ethanol, t-butanol, water, and mixtures thereof. The lipid ingredients are dissolved in the lipid solvent.

The initial concentration of lipid ingredients dissolved in the lipid solvent, such as ethanol, may be in the range of about 0.33 to about 1.0 g/L. The lipid solution may be prepared apart from the manufacturing process discussed herein.

The mixture of the fluticasone furoate and the lipid solvent forms the lipid solution. The drug to lipid ratio may be controlled by varying the amount of lipid ingredients and fluticasone furoate. Optionally, mildly heating the lipid solvent may aid in mixing together the lipid ingredients and fluticasone furoate. This mixing process can result in efficient encapsulation of fluticasone furoate into multi-lamellar vesicles.

The weight ratio of lipid to drug increases the stability of the liposome formulation without significantly compromising delivery. This process permits the drug to lipid ratio to be varied in the range of about 1:10 to about 1:40 by weight, preferably in the range of about 1:10 to about 1:20. In one embodiment, the liposome formulation may be added to fluticasone furoate at a ratio of about 15 parts lipid ingredients to about 1 part fluticasone furoate. In another embodiment, the liposome formulation may be added to fluticasone furoate solution at a ratio of about 10 parts lipid ingredients to about 1 part fluticasone furoate.

In accordance with the above description, in an embodiment, the formulation is prepared by (1) mixing fluticasone furoate with lipid ingredients comprising DPPC and cholesterol in a molar ratio of about 1:1, and a mass ratio of fluticasone furoate to lipid ingredients in the range of about 1:10 to about 1:40; (2) injecting the mixture into normal saline solution to form liposome vesicles; and (3) ultrafiltration and concentration of the resulting liposome vesicles-containing solution.

Another aspect of this invention is a liposome formulation made in accordance with the preparation steps described above, wherein the formulation comprises DPPC and cholesterol in a molar ratio of about 1:1, and a mass ratio of fluticasone furoate to lipid ingredients in the range of about 1:10 to about 1:40, which is prepared by the following steps: (1) mixing fluticasone furoate with lipid ingredients comprising DPPC and cholesterol in a molar ratio of about 1:1 and a mass ratio of fluticasone furoate to lipid ingredients in the range of about 1:10 to about 1:40, (2) injecting the mixture into normal saline solution to form liposome vesicles, and (3) ultrafiltration and concentration of the resulting liposome vesicles-containing solution. This preparation produces a liposome formulation having useful characteristics and features as described above, including a pH value ranging between about 4.0 and about 7.0.

The following examples are intended to illustrate and exemplify the various aspects of carrying out the present invention and are not intended to limit the invention in any way.

Example 1

Preparation of 10 ml Liposomal Formulation:
Initial total volume: 100 ml;
Ethanol volume: 30%;
Lipid ingredients: DPPC, cholesterol;
Initial lipid ingredients: 0.3 mg/ml;
Initial fluticasone furoate: 0.01 mg/ml;
Final volume: 10 ml;
Preparation Steps:
(1) mixing fluticasone furoate with lipid ingredients:
  19.6 mg of DPPC and 10.4 mg of cholesterol were weighed into 30 ml of ethanol, which was heated to a temperature of 50° C. in a beaker, and mixed until completely dissolved to provide a lipid solution. Then 1 mg of fluticasone furoate was added to the lipid solution, and the solution was stirred until completely dissolved.
(2) injecting the mixture into normal saline solution to form liposome vesicles:
The lipid solution containing fluticasone furoate was added to 50 ml of normal saline and mixed for 20 minutes until dissolved. After that, the solution was transferred into a 100 ml volumetric flask, and the flask was made to volume with normal saline.
(3) ultrafiltration and concentration:
  A peristaltic pump was connected to a hollow fiber cartridge for ultrafiltration and concentration. The sample liposome formulation was pumped through the cartridge for ultrafiltration.

Example 2

In accordance with the preparation method described above, six different samples were prepared with high encapsulation efficiency and different drug to lipid ratios. The encapsulation efficiency of six samples was over 80%, and the encapsulation efficiency of sample 5 was more than 90%. The average particle size was in the range of 130 nm-160 nm.

Sample 1: 6.5 mg DPPC and 3.5 mg cholesterol were weighed into 30 ml of ethanol, which was heated to a temperature of 50° C. in a beaker, and mixed until completely dissolved to provide a lipid solution. Then 1 mg of fluticasone furoate was added to the lipid solution, and the solution was stirred until completely dissolved. The lipid solution containing fluticasone furoate was then added to 50 ml of normal saline and stirred for 20 minutes until completely dissolved. After that, the solution was transferred into a 100 ml volumetric flask, and the flask was made to volume with normal saline. The liposome formulation was concentrated to a volume of 10 mL.

Sample 2: 9.8 mg DPPC and 5.2 mg cholesterol were weighed into 30 ml of ethanol, which was heated to a temperature of 50° C. in a beaker, and mixed until completely dissolved to provide a lipid solution. Then 1 mg of fluticasone furoate was added to the lipid solution, and the solution was stirred until completely dissolved. The lipid solution containing fluticasone furoate was then added to 50 ml normal saline and stirred for 20 minutes until completely dissolved. After that, the solution was transferred into a 100 ml volumetric flask, and the flask was made to volume with normal saline. The liposome formulation was concentrated to a volume of 10 mL.

Sample 3: 13.1 mg DPPC and 6.9 mg cholesterol were weighed into 30 ml of ethanol, which was heated to a temperature of 50° C. in a beaker, and mixed until completely dissolved to provide a lipid solution. Then 1 mg of fluticasone furoate was added to the lipid solution, and the solution was stirred until completely dissolved. The lipid solution containing fluticasone furoate was then added to 50 ml normal saline and stirred for 20 minutes until completely dissolved. After that, the solution was transferred into a 100 ml volumetric flask, and the flask was made to volume with normal saline. The liposome formulation was concentrated to a volume of 10 mL.

Sample 4: 16.4 mg DPPC and 8.6 mg cholesterol were weighed into 30 ml of ethanol, which was heated to a temperature of 50° C. in a beaker, and mixed until completely dissolved to provide a lipid solution. Then 1 mg of fluticasone furoate was added to the lipid solution, and the solution was stirred until completely dissolved. The lipid solution containing fluticasone furoate was added to 50 ml normal saline and stirred for 20 minutes until completely dissolved. After that, the solution was transferred into a 100 ml volumetric flask, and the flask was made to volume with normal saline. The liposome formulation was concentrated to a volume of 10 mL.

Sample 5: 19.6 mg DPPC and 10.4 mg cholesterol were weighed into 30 ml of ethanol, which was heated to a temperature of 50° C. in a beaker, and mixed until completely dissolved to provide a lipid solution. Then 1 mg of fluticasone furoate was added to the lipid solution, and the solution was stirred until completely dissolved. The lipid solution containing fluticasone furoate was then added to 50 ml normal saline and stirred for 20 minutes until completely dissolved. After that, the solution was transferred into a 100 ml volumetric flask, and the flask was made to volume with normal saline. The liposome formulation was concentrated to a volume of 10 mL.

Sample 6: 26.2 mg DPPC and 13.8 mg cholesterol were weighed into 30 ml of ethanol, which was heated to a temperature of 50° C. in a beaker, and mixed until completely dissolved to provide a lipid solution. Then 1 mg of fluticasone furoate was added to the lipid solution, and the solution was stirred until completely dissolved. The lipid solution containing fluticasone furoate was then added to 50 ml normal saline and stirred for 20 minutes until completely dissolved. After that, the solution was transferred into a 100 ml volumetric flask, and the flask was made to volume with normal saline. The liposome formulation was concentrated to a volume of 10 mL. The results are shown in table 1 and table 2.

TABLE 1

Sample parameters

| Parameter | Sample 1 | Sample 2 | Sample 3 | Sample 4 | Sample 5 | Sample 6 |
|---|---|---|---|---|---|---|
| Drug to lipid ratio | 1:10 | 1:15 | 1:20 | 1:25 | 1:30 | 1:40 |
| Total concentration of fluticasone furoate (mg/100 ml) | 1.003 | 1.051 | 1.013 | 0.939 | 1.069 | 0.95 |
| Concentration of free fluticasone furoate (mg/100 ml) | 0.164 | 0.194 | 0.194 | 0.122 | 0.107 | 0.17 |
| Encapsulation efficiency (%) | 83.67 | 81.58 | 80.88 | 86.99 | 90.01 | 82.08 |

TABLE 2

Physical and chemical properties of the samples

| Physical & chemical properties | Sample 1 | Sample 2 | Sample 3 | Sample 4 | Sample 5 | Sample 6 |
|---|---|---|---|---|---|---|
| Appearance | Whitish suspension | Whitish suspension | Whitish suspension | Whitish suspension | Whitish suspension | Whitish suspension |
| Average particle size (nm) | 150.8 | 146.0 | 147.6 | 144.9 | 130.5 | 173.1 |
| pH | 5.42 | 5.72 | 5.36 | 5.31 | 5.72 | 6.22 |

Example 3

Sample 5 was sprayed using an ultrasonic vibrating mesh nebulizer and a compressed air nebulizer. Malvern Spraytec was used to measure the particle size distribution of the droplets. The particle size distribution of the droplets is expressed in terms of D10, D50 and D90. As shown in table 3, the D50 values of the droplets formed with both the compressed air nebulizer and the ultrasonic vibrating mesh nebulizer were less than 5 µm, and the D90 values of the droplets formed with both the compressed air nebulizer and the ultrasonic vibrating mesh nebulizer were less than 12 µm.

TABLE 3

Particle size distribution from different types of nebulizer

| Sample Number | Nebulizer | D10 | D50 | D90 |
|---|---|---|---|---|
| Sample 5 | Compressed air nebulizer | 1.694 µm | 4.828 µm | 11.16 µm |
| | Ultrasonic vibrating mesh nebulizer | 2.086 µm | 3.945 µm | 7.295 µm |

While various embodiments of the present invention have been described above, it should be understood that they have been presented by way of example only, and not limitation. For example, the present invention is not limited to the physical arrangements or dimensions illustrated or described. Nor is the present invention limited to any particular design or materials of construction. As such, the breadth and scope of the present invention should not be limited to any of the above-described exemplary embodiments, but should be defined only in accordance with the following claims and their equivalents.

What is claimed is:

1. A formulation comprising a suspension of a plurality of liposomes in a solvent, wherein the liposomes comprise a lipid ingredient that encapsulates fluticasone furoate, wherein the lipid ingredient comprises DPPC and cholesterol in a DPPC:cholesterol molar ratio of about 0.8:1 to about 1.2:1, the weight ratio of fluticasone furoate to lipid ingredient is about 1:30, the concentration of fluticasone furoate is about 1 mg/100 mL, and the solvent is normal saline.

2. The formulation according to claim 1, wherein the liposomes have an average size of about 130 nm.

3. The formulation according to claim 1, having a pH ranging from about 4.0 to about 7.0.

4. The formulation according to claim 1, wherein the composition has a pH of about 5.7.

5. The formulation according to claim 1, wherein the composition has an encapsulation efficiency of at least 90%.

6. The formulation according to claim 1, wherein the formulation when nebulized forms droplets with a D50 value ranging from about 3.9 µm to about 4.8 µm.

7. The formulation according to claim 1, wherein the formulation when nebulized forms droplets with a D90 value ranging from about 7.3 µm to about 11.2 µm.

8. The formulation according to claim 1, further comprising an antioxidant selected from the group consisting of a water-soluble antioxidant and an oil-soluble antioxidant.

9. The formulation according to claim 8, wherein the oil-soluble antioxidant is selected from the group consisting of alpha-tocopherol, alpha-tocopherol succinate, alpha-tocopherol acetate and mixtures thereof, and the water-soluble antioxidant is selected from the group consisting of ascorbic acid, sodium bisulfate, sodium sulfite, sodium pyrosulfite, L-cysteine, and mixtures thereof.

10. A method of preparing the formulation of claim 1 comprising:
  (1) dissolving fluticasone furoate, DPPC, and cholesterol in ethanol, wherein the fluticasone furoate is present in an amount of about 1 mg/30 mL of ethanol, the DPPC is present in an amount of about 19.6 mg/30 mL of ethanol, and the cholesterol is present in about 10.4 mg/30 mL of ethanol, to provide a first mixture;
  (2) injecting the first mixture into a normal saline solution with stirring, wherein the ratio of the first mixture to the saline solution is about 30:50 (v/v) to form a second mixture comprising liposome vesicles;
  (3) adding normal saline to the second mixture comprising liposome vesicles in an amount sufficient to provide a volume of about 100 mL for each 30 mL of ethanol to provide a third mixture; and
  (4) ultrafiltering and concentrating the third mixture to a volume of 10 mL per each 100 mL of the third mixture to provide the formulation.

11. The method according to claim 10, wherein the formulation has a pH ranging from about 4.0 to about 7.0.

12. The method of claim 10, wherein the first mixture is heated to a temperature ranging from about 40° C. to about 80° C.

13. The method of claim 11, wherein the first mixture is heated to a temperature of about 50° C.

14. The method of claim 10, wherein the ultrafiltering uses a hollow fiber membrane.

* * * * *